United States Patent
Kühni et al.

(10) Patent No.: US 12,266,437 B2
(45) Date of Patent: Apr. 1, 2025

(54) SECURE DRUG DELIVERY DATA TRANSMISSION

(71) Applicant: Ypsomed AG, Burgdorf (CH)

(72) Inventors: Florian Kühni, Bern (CH); Dominik Reubi, Bern (CH); Andreas Schneider, Bern (CH); Simon Schüpbach, Bern (CH)

(73) Assignee: Ypsomed AG, Burgdorf (CH)

( * ) Notice: Subject to any disclaimer, the term of this patent is extended or adjusted under 35 U.S.C. 154(b) by 722 days.

(21) Appl. No.: 17/514,281

(22) Filed: Oct. 29, 2021

(65) Prior Publication Data

US 2022/0051778 A1 Feb. 17, 2022

Related U.S. Application Data

(63) Continuation of application No. PCT/EP2020/061660, filed on Apr. 28, 2020.

(30) Foreign Application Priority Data

Apr. 30, 2019 (EP) .................................... 19172037

(51) Int. Cl.
*G16H 20/17* (2018.01)
*G06F 21/62* (2013.01)
*G06N 3/08* (2023.01)

(52) U.S. Cl.
CPC ......... *G16H 20/17* (2018.01); *G06F 21/6245* (2013.01); *G06N 3/08* (2013.01)

(58) Field of Classification Search
CPC ...................................................... G16H 20/17
See application file for complete search history.

(56) References Cited

U.S. PATENT DOCUMENTS

| 9,980,140 | B1 * | 5/2018 | Spencer | ................ H04W 12/02 |
| 2007/0254593 | A1 * | 11/2007 | Jollota | ................... G16H 40/67 |
| | | | | 455/67.11 |

(Continued)

FOREIGN PATENT DOCUMENTS

| EP | 3381493 A1 | 10/2018 |
| EP | 3476417 A1 | 5/2019 |

(Continued)

OTHER PUBLICATIONS

International Preliminary Report on Patentability received for International Application No. PCT/EP2020/061660, mailed on Nov. 2, 2021, 14 pages.

(Continued)

*Primary Examiner* — Evangeline Barr
(74) *Attorney, Agent, or Firm* — Dorsey & Whitney LLP (57) ABSTRACT

The disclosure is concerned with privacy and integrity of personalized protected health information when transmitted to a cloud computing facility and subsequently distributed to a plurality of stakeholders. An electronic unit of a drug delivery device is configured to prepare payload data comprising data items according to an allocation scheme, and to encrypt, based on an encryption key, and transmit data including the payload data. The allocation scheme and the encryption key are defined for each of a plurality of data subscribers. Accordingly, personalized protected health information payload data is suitably protected with generator-to-subscriber or pass-through data security measures, and any intermediary node or data server in the communication network lacking a matching decryption key will not have access to unencrypted payload data.

10 Claims, 3 Drawing Sheets

(56) References Cited

U.S. PATENT DOCUMENTS

| | | | |
|---|---|---|---|
| 2010/0222847 A1 | 9/2010 | Goetz | |
| 2012/0191384 A1 | 7/2012 | Kalgren et al. | |
| 2016/0268954 A1 | 9/2016 | Favreau | |
| 2017/0235920 A1* | 8/2017 | Bauss | G16H 40/63 705/2 |
| 2017/0288857 A1 | 10/2017 | Zuhorski et al. | |
| 2018/0236181 A1 | 8/2018 | Marlin et al. | |
| 2019/0388619 A1* | 12/2019 | Hammen | A61M 5/31593 |
| 2020/0228161 A1* | 7/2020 | Tsiaflakis | H04B 3/32 |
| 2021/0038833 A1* | 2/2021 | Schauderna | A61M 5/3157 |

FOREIGN PATENT DOCUMENTS

| | | |
|---|---|---|
| EP | 3734605 A1 | 11/2020 |
| WO | 2007107564 A1 | 9/2007 |
| WO | 2018138192 A1 | 8/2018 |
| WO | 2019224626 A1 | 11/2019 |
| WO | 2020221707 A1 | 11/2020 |

OTHER PUBLICATIONS

Extended European Search Report issued in European Patent Application 19172037.4, mailed on Nov. 7, 2019, 8 pages.

International Search Report and Written Opinion issued in International Application No. PCT/EP2020/061660, mailed on Oct. 23, 2020, 19 pages.

* cited by examiner

| Subscriber\\Data item | Device mfr. | Drug suppl. | HCP | CRO | Insurance | Patient |
|---|---|---|---|---|---|---|
| Device-ID | x | | | | | |
| UDI | | x | x | x | x | x |
| Therapy plan | | | x | x | | x |
| Study-ID | | | x | x | | |
| Patient-ID Anonymized | | | | x | | |
| Medicament | | | x | x | x | x |
| Injection-Time | | x | x | x | | x |
| Injection-Result | | x | x | x | x | x |
| Injection-Dose | | | x | x | | x |
| Quality Indicator QI | x | | | | | |
| Drug Temperature | | | | | | x |
| Device-Battery | x | | | | | x |
| Device-Error | x | | | | | x |
| Device-Firmware | x | | | | | |

SECURE DRUG DELIVERY DATA TRANSMISSION

CROSS REFERENCE TO RELATED APPLICATIONS

This application claims priority to International Patent Application No. PCT/EP2020/061660, filed Apr. 28, 2020, entitled "SECURE DRUG DELIVERY DATA TRANSMISSION", which in turn claims priority to European Patent Application No. 19172037.4, filed Apr. 30, 2019, entitled "SECURE DRUG DELIVERY DATA TRANSMISSION", each of which is incorporated by reference herein, in the entirety and for all purposes.

TECHNICAL FIELD

The present disclosure relates to medicament delivery devices for delivering, administering, dispensing, injecting, or infusing substances and/or liquids such as insulin or hormone preparations. It involves an electronic unit incorporated in, or attachable to, a delivery device, and includes at least one sensor for monitoring a delivery process executed by means of the delivery device in the context of a drug delivery monitoring system.

BACKGROUND

A variety of diseases exist that require regular treatment by parenteral subcutaneous or intra-muscular administration of a drug or medicament, and a number of drug delivery devices have been developed to support a patient in accurately and controllably delivering an amount of drug in a self-administration process. Delivery devices include injection devices that are removed from the injection site after each drug delivery event or medication process. An injection pen device has an elongate device body defining a longitudinal main device axis. The term "distal end" refers to the end of the injection device where an injection needle is located, the term "proximal end" designates the opposite end thereof. Delivery devices further include infusion devices or pumping devices for continual delivery of a regular or basal amount of medication through a fluid channel into the body of the patient, wherein the fluid channel remains in use for a prolonged period of time.

Disposable or single-use delivery devices are adapted to deliver a drug from a container such as a pre-filled syringe that is not intended to be replaced or refilled by the patient. Reusable, semi-reusable, or hybrid delivery devices have a container that may be replaced by the patient, or a cartridge that may be refilled, while some components of the device may be reused with the replaced or refilled drug container. An automatic injection device has an electric motor or a drive spring for biasing a piston rod and shifting a piston in a container barrel, wherein the drive spring may have to be tensioned or loaded manually prior to injection of a dose. A manually powered injection device requires a user to provide manually the energy to move the piston, for instance by applying a distal force component to the injection device.

By way of example, diabetes may be treated by self-administration of insulin with the help of multi-variable-dose insulin injection pens. The insulin dose to be injected may typically be manually selected by turning a dosage knob and observing the actual dialed dose in a dose window or display of the insulin pen. A dose is dispensed by inserting the needle into a suitable portion of human skin and by moving the piston manually or by actuating a release of an automatic injection device.

Drug delivery device based therapies generally benefit from an electronic unit or control unit embedded or integrated in the delivery device, or being part of an auxiliary or supplemental electronic module or add-on device detachably attached to the delivery device. The electronic unit monitors a drug delivery process, in order to proactively prevent incorrect handling of the device and/or to keep track of the doses already applied, and generates data related to an instantaneous condition and/or use of the delivery device. Suitable sensors of the electronic unit are configured to detect a status or signal from any kind of indicating component of the delivery device, including user interface elements and actuators. A wireless communication unit of the electronic unit is provided to wirelessly communicate, for example, upload, drug delivery information to a nearby mobile device or dedicated medical gateway. The drug delivery information includes at least a time stamp and the expelled dose, indicative of a time of a medication event and of a quantity of delivered medicament. The drug delivery information may be transmitted instantaneously, or stored in a memory unit connected to the processing unit, for later upload or batch transfer.

WO 2007/107564 A1 proposes to record acoustic signals or vibration signals that may be associated with a dose delivery of the medication or to a dose adjustment process. If a detected "click-sound" falls within a low frequency range, a unit dose of medicament is being set. Similarly, if the detected "click-sounds" fall within a high frequency range, a dose of medicament is being expelled from the medication delivery device. By counting the number of clicks during an expel sequence, the amount of medicament expelled from the medicament delivery device can easily be calculated.

The use of an auxiliary electronic module may be advantageous over embedded electronic units, not least in retrofit configurations with an existing design of a disposable injection device that is not available for the inclusion of sensors and electronics. The disposable injection device preferably is an auto-injector, a patch injector, a variable dose injection pen, or any other injection device for delivering a fixed or variable dose of a drug from a container that is not intended to be replaced by the patient.

EP 3476417 A1 describes a medical monitoring system including a disposable injection device with a container holder for holding a container or reservoir such as a cartridge or a syringe comprising a liquid drug for subcutaneous or intramuscular injection. The system further includes a passive machine-readable tag mounted to, for instance embedded in or attached to a surface of, a device housing of the injection device and coding or storing drug information about the drug comprised in the container. The drug information includes any or all of a drug identifier, an expiry date, or a batch number of the drug, medicament, or active ingredient contained in the container. The system also includes an electronic module adapted to be releasably attached to the injection device and comprising a tag reader different from the drug delivery sensing means, for reading the drug information from the machine-readable tag. The system ultimately includes a drug status signaling or interfacing unit for signaling to a user a drug status that is based on, or derived from, the drug information.

In the context of healthcare data management, it is advisable or even mandatory to treat drug delivery data that has been collected by any kind of electronic monitoring unit, as Protected Health Information (PHI). In order to avoid data abuse, misappropriation, manipulation or the like to the detriment of the patient or a healthcare provider, several measures may be envisaged. In the following, personally identifiable patient adherence data is referred to as the monitoring data accumulated by the electronic unit, including records of time-stamped delivery events, and possibly including a log or transcript of a bidirectional interaction between patient and electronic device, including in particular any feedback or recommendation provided to the user. Communication of such patient adherence data to a remote site has to guarantee privacy and integrity of the data. Specifically, communications containing PHI or equivalent patient adherence data and transmitted electronically over open networks have to be encrypted and protected from being intercepted by anyone other than the intended recipient.

WO 2018/138192 discloses flexible carrier-foil based smart labels that can be transferred physically as part of a fluid delivery system item between multiple entities in a healthcare continuum, i.e., from a medicament supplier to a healthcare provider to a patient. Each entity in turn encrypts and stores data tuples (data structures that store an ordered sequence of values) of the system item owned by, or assigned to, the entity in a central database or cloud-based data repository. Communicating entities perform a one-time exchange of cryptographic keys valid for any system item or data tuple for sharing of their respective data.

U.S. Pat. No. 9,980,140 B1 discloses a medical device and a server system using pass-through encryption techniques to establish end-to-end encryption between the medical device and the server system, which prevents any intermediary devices or nodes in the communication path, for example a mobile device, from reading the information that is transmitted between the medical device and the server system. Such pass-through encryption between the medical device and the server system can be performed by using public and private encryption keys for the server system, with a public key of the latter being available at the medical device.

PHI may be uploaded or transferred as encrypted payload data to a duly protected information technology server system, such as a computing cloud or distributed data server structure, and stored in this server system for subsequent redistribution. The patient adherence data may specifically be stored in an encrypted format that restricts access for detailed data analysis to a trusted expert holding a particular key. In case of several trusted experts, the management of the keys and content is handled by the server system, which provides maximum flexibility with regards to analysis of PHI, and even enables patients to use a web-based interface to access their data.

In the present context, the terms "substance", "drug", "medicament" and "medication" are to be understood to include any flowable medical formulation suitable for controlled administration through a means, such as, for example, a cannula or a hollow needle, and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

SUMMARY

It is an objective of the disclosure to enable secure, flexible and cost-effective operation of components, devices and systems for the generation, collection and transmission of delivery data associated with the use of drug delivery devices. It is another objective of the disclosure to increase and improve privacy and integrity of personalized protected health information when transmitted to a cloud computing facility and subsequently distributed to a plurality of stakeholders. These objectives may be achieved by an electronic unit and by a method of monitoring drug delivery and capturing such data for selective transmission to specific subscribers according to the claims herein. Various embodiments are evident from the claims and disclosure.

According to the disclosure, an electronic unit may be associated with a drug delivery device holding a container with a liquid drug as, either, an embedded part of an electronic delivery device, or as a reusable electronic module attachable to a delivery device which itself may be free of integrated sensors and/or electronics. The electronic unit may include sensors and processor means to generate, or obtain/collect, and to handle, or process, delivery data, including drug data related to the drug comprised in a container of the delivery device, device or module data related to a property of the delivery device or the electronic module, and event data related to an individual delivery event or process executed by means of the delivery device. The delivery data may include plural data items, or data classes, each having a distinct origin and associated update regime (or subscription), and with a data item instance, or value, of an event data item being updated at or after each delivery event. The electronic unit may include transmitter means to transmit data items to a first data subscriber and a second data subscriber, including to a manufacturer of the electronic unit and/or of the drug delivery device, a drug-producing pharmaceutical company, a Health Care Professional (HCP), a Clinical Research Organization (CRO), a health insurance company, or the patient himself/herself, as the primary stakeholders or entities of an integrated healthcare data management system.

The present disclosure improves over the prior art by collecting and storing the sensed, generated or otherwise obtained drug delivery data and related data available to the electronic unit in a manner that associates a specific encryption key and specific data with each of two or more particular subscribers via a compact and well-defined data structure that facilitates control and secure delivery of periodic encrypted data transmission events, e.g., subscriptions. The electronic unit may have access to a repository such as a memory having stored a first and a second encryption key associated with the first and second data subscriber, respectively, such as a subscriber-provided public key for which a matching private key is held by the subscriber, or any kind of shared secret exclusively accessible to the electronic unit and the subscriber. The electronic unit may have access to a repository having stored a first data allocation scheme, and a second data allocation scheme, e.g., a data structure (for example, a table), indicating to which data item(s) the first and second data subscriber has respectively subscribed. The allocation schemes may define non-identical subsets of delivery data, differing in at least one data item. This may improve the electronic unit's ability to offer a data structure-based specification of the data in a subscription for at least the first and second data subscriber. The electronic unit may be configured to prepare a frame, or package, or packet of first transmit data including first payload data comprising data items according to the first allocation scheme, and to encrypt the first transmit data based on the first encryption key, such that decryption of the first payload data is not possible without possession of a decryption key matching the first encryption key, such as the private key matching the public key of the first subscriber. The electronic unit may be configured to prepare a frame, or package, or packet of second transmit data including second payload data comprising data items according to the second allocation scheme, and to encrypt the second transmit data based on the second encryption key, such that decryption of the second payload data is not possible without possession of a decryption key matching the second encryption key, such as the private key matching the public key of the second subscriber. The encrypted first and second transmit data may be sent by the transmitter of the electronic unit into a communication network and to or towards the first and second subscriber. This improved data structure organizing and storage approach may easily be scaled up from the first and second subscribers to a larger number of subscribers; it also can facilitate changes in the subscribed-to data of the subscribers.

The first and second payload data may comprise aggregated, or merged, instances of respective data items listed in the first and second allocation scheme. Payload data may be included into subscriber-defined transmit data packets that are suitably protected with end-to-end or pass-through data security measures as an effective means of increasing and thus improving object security. Encryption of payload data may take place right at the electronic unit where the delivery data, in particular event data, is generated in the first place. Channel or transmission layer security requirements may thus be relaxed; any intermediary node or data server in the communication network, as well as any subscriber lacking the matching decryption key, may not have access to unencrypted payload data. Data security concerns related to a pairing routine between the electronic unit and an adjacent or associated mobile or gateway device of the communication network may likewise be mitigated by the proposed data generator-to-subscriber encryption. The procedure may flexibly be expanded to include further subscribers, and the allocation scheme and even the encryption key of each subscriber may be changed at any time. The payload data may be prepared on behalf of, and forwarded to, all subscribers concurrently at the end of each delivery event. Alternatively, payload data may be aggregated over several successive delivery events performed by a same delivery device and forwarded at a certain rate, i.e., once per day or week, which rate may be subscriber-dependent. Still alternatively, payload data may only be forwarded to subscriber A if and when a data item instance of a data item in the allocation scheme of subscriber A has changed. Accordingly, also the manufacturer of the electronic unit and/or of the drug delivery device and the drug-producing pharmaceutical company may repeatedly receive data item updates during the entire life-cycle of the delivery device by such a subscription. In one embodiment, the delivery device may be a disposable delivery device such as an auto-injector or variable-dose injection pen for which the drug container or reservoir may be pre-filled with liquid and not intended to be replaced or refilled by the patient. The electronic unit may be part of an auxiliary electronic module, or add-on, attachable to the delivery device. Movable parts within the delivery device generate delivery signals that are detected by an injection sensor of the electronic unit. The device comprises a machine-readable tag or label on which may be stored, or encoded, an identifier and the first encryption key of the first data subscriber. The electronic module may include a tag reader for reading the identifier as well as the first encryption key from the tag. The first encryption key, in one example a shared secret, may therefore be copied to a mobile data memory means and conveniently provided to the end-assembly site of the delivery device, and may not need to be managed by a key server nor transit via potentially unsecure communication networks. The first encryption key may be a single-use shared-secret that is specific to, and seamlessly renewed with each exchange of, the disposable delivery device.

In an alternative embodiment, the delivery device may be a reusable injection device with a possibility to refill or replace an empty cartridge by the patient. The electronic unit may be embedded in the injection device, such that the device qualifies as an electronic, or intelligent, injection device. The subscriber-based encryption key, in particular a public key of an asymmetric key pair, may be provided to the electronic unit in an appropriate way via the communication network and corresponding receiver of the electronic unit.

In another variant the electronic unit may be configured to encrypt the first payload data with the first encryption key, and to transmit the encrypted first payload data. In this variant, a transmit data package comprises the encrypted first payload data plus extra data limited to network routing information. In an alternative variant, the first payload data may be encrypted with a generic key and the generic key may be encrypted with the first encryption key, wherein the generic key may be a single-use key generated by the electronic unit. In this variant, a transmit data package comprises the encrypted first payload data and the encrypted generic key, as well as indispensable routing information. The first data subscriber receiving such transmit data package will first decrypt the generic key with the aid of the matching decryption key, and subsequently decrypt the encrypted first payload data with the generic key.

In a further embodiment, the electronic unit may include memory as a local repository storing the encryption key and the data allocation scheme for immediate access by a processor of the electronic unit, and irrespective of how the key and scheme or data structure have been provided to the electronic unit.

In a still further embodiment, the first data allocation scheme may assign to a manufacturer of the electronic unit as the first subscriber, a first selection of data items of the delivery data, including an identifier, or serial number, and a battery level of the electronic unit, or of the electronic module or delivery device embedding the electronic unit. Such device or module data together with selected delivery event data (including sensed, collected and/or generated data) may allow the manufacturer to track a life-cycle and/or health status of the electronic device or module.

According to the disclosure, in a method of monitoring drug delivery, an electronic unit may be adapted to generate or sense and handle delivery data related to a device, a drug, and/or an individual delivery event including dispensing of a dose of drug by means of a drug delivery device to which the electronic unit is associated. The delivery data may include a plurality of data items of which distinct subsets are transmitted to a first and a second data subscriber. The method may include the following steps:
- By the first and the second subscriber, generating respectively a first and second encryption key and defining a first and a second data allocation scheme indicative of which data item(s) the first and second data subscriber have respectively subscribed to.
- Providing, or forwarding, the first and second encryption key and the first and second data allocation scheme to a memory of the electronic unit.
- By the electronic unit, preparing first transmit data including values of data items according to the first data allocation scheme, and encrypting the first transmit data based on the first encryption key.
- By the electronic unit, preparing second transmit data including values of data items according to the second data allocation scheme, and encrypting the second transmit data based on the second encryption key.

In a refined variant of the method, a transmitter of the electronic unit may transmit the encrypted first and second transmit data to a computing cloud or distributed data server structure as a single or unified repository for all transmit data. From the data server, the encrypted first transmit data may be provided to the first subscriber, and the encrypted second transmit data is provided to the second subscriber, both according to individual needs either upon request or based on a regular schedule. A data retention policy agreed between data provider and data subscriber may define how long the uploaded data will be available for download by the subscriber, and/or whether or not the data is erased upon download.

WO 2019224626 A1 discloses an auxiliary electronic module for a variable-dose injection device generating a number of click sounds proportionate to a dose of medicament. The electronic module comprises sensor elements including one or more of an acceleration sensor, a gyroscope sensor, a piezoelectric contact microphone sensor, and a force or pressure transducer, for sensing tactile and/or acoustic vibrations that are generated in the injection device in the form of individual clicks for each dose unit during dialing and/or dispensing of a dose. From a signal of the sensor elements recorded as a device feedback sample signal or suspected dose-unit click sound, multiple features or characteristics are derived, such as a sum of correlation values of a test signal with single-axis gyroscope signals, or a sum of absolute derivatives of single-axis gyroscope signals. These features are evaluated in a scatter plot of a multi-dimensional feature space or otherwise classified by a classifier to assign the device feedback sample signal to a device feedback class such as a Dial-Up Click, a Dial-Down Click, an Injection Click, or a Non-Click feedback. Various types of classifiers exist and may be employed, such as a Support Vector Machine (SVM) with a linear kernel, a Feed Forward Artificial Neural Network (ANN), or a Gradient boost decision tree Neural Network. WO 2019224626 A1 (applicant Ypsomed AG) is incorporated herein for all purposes by way of reference.

In one variant of the disclosure, a classification probability lower than one is introduced to account for the fact that the classification of a device feedback sample signal into one of the feedback classes as disclosed in WO 2019224626 A1 may not be unequivocal. In other words, the identification of a particular feedback sample signal as an Injection Click may be most probable yet accompanied by a small classification uncertainty. From the individual classification probabilities of all device feedback sample signals of a particular delivery event into one of the device feedback classes, a quality indicator or trust parameter may be derived to indicate a probability that the value of a dispensed dose reported for the particular delivery event is accurate and reflects the amount of liquid actually dispensed by the device. The quality indicator may also be seen as a measure of an error or uncertainty related to the value of the dispensed dose and/or other event data. The event data sensing quality indicator may for instance be defined as an average, or as the lowest classification probability value, of the individual classification probabilities of the identified dose units into the device feedback classes. The quality indicator of the delivery event may also reflect a possible mismatch between the individually determined number of dialed and dispensed dose units, or an uncertainty related to the identification of a priming event. Alternative or complementary to the classification probability, a variance in the multi-dimensional scatter plot evaluation of the features may be the individual feedback sample signal contribution to the quality indicator. In case the individual dose units are determined from the feedback sample signals by other click-identification algorithms, schemes, filters or the like, a time constant in a relaxing sensor signal, or a sensor signal difference to a threshold value, are exemplary contributions to the quality indicator. Still alternatively, the event data sensing quality indicator may be derived from other aspects of the sensor signal independent of, or common to, the individual feedback sample signals. A correlation between two concurrent feedback sample signals from two distinct sensors of the electronic unit may also be a basis for a quality indicator. A delivery event data quality indicator may be determined for virtually any type of mechanical, electrical, optical, or acoustic sensor element, and regardless of whether the latter is part of an electronic unit embedded in an electronic auxiliary module or in an electronic delivery device. Thus, the present disclosure also includes an improvement in delivery data reporting by providing a sequence of quality indicator data that allows the subscriber to perform analysis using a time sequence of such data to determine or predict certain device and/or electronic module points of failure. The predictions may enable interventions to defer or prevent the predicted failure of the electronic unit, for instance causing the electronic module to be reprogrammed as described herein.

Event data related to an individual delivery event, medication process, or use cycle executed by means of the injection device or the electronic delivery device may include, in addition to the number of dispense clicks of the delivery event and the above event data sensing quality indicator, a total number of identified clicks of the device, a total number of delivery events of the device, a time elapsed since a last battery recharge, and a remaining battery level of the battery of the electronic unit. On that basis, quality indicators may also be suitably scaled, i.e., divided by the number of use cycles or battery recharges, before comparing across modules or devices. The manufacturer of the electronic modules or the electronic delivery devices maintains a repository of information, also known as digital twins, about all modules and devices. The manufacturer may derive and track, from the event data received, aspects related to health (battery, firmware, in-use, errors), performance, and lifecycle (shipped, activated, retired) of individual items, and arrange for replacement of faulty modules or devices.

A temporal evolution of the quality indicator for successive delivery events executed with a same injection device or at least monitored with a same electronic module attached to distinct injection devices, may be evaluated. A trend or change in the quality indicator over time, or a trend in any statistical measure of the quality indicator such as variance, in particular a deterioration thereof, may, by the successive data transmissions under a subscriber's subscription, be identified and extrapolated in a suitable way to determine or predict a point of failure of the module and/or a time of insufficient event data sensing quality of the electronic unit. The root cause for such evolution may reside in the properties of the mechanical components of the injection device and/or in the performance of the sensor element. From a deteriorating correlation between two concurrent sensor signals from two distinct sensors one may infer that one of the sensors is malfunctioning. The root cause may include component aging, such as silicone deterioration in the lubrication layer between a piston and a container barrel, corrosion of electrically conducting contact elements, or general material fatigue. The root cause may also reside in handlings errors, for instance if a label on the surface of the injection device is damaged, or if a sticker or other extra element is applied to the surface of the injection device, resulting in repeated misalignment of the sensor elements in the case of an electronic module no longer being attached properly.

Irrespective of the actual root cause, and independent of a battery level of the electronic unit and an amount of liquid left in the container, the observed deterioration detectable with a subscription to periodic or sequential data improved as described herein may be countered by acts of predictive or proactive maintenance, in due time before the electronic module is anticipated to actually fail. The acts of predictive maintenance may include a replacement of the electronic module, or of the batch of injection devices to which the electronic module is attached, which includes shipping a new electronic module or a set of injection devices from a different batch to the user. Maintenance may also involve a reconfiguration or recalibration of a software element used by the electronic unit to determine a dispensed dose, in particular a software element including the above device feedback sample signal classifier or any other click-identification algorithm, scheme, filter or the like. A classifier or other algorithm based on a Neural Network may be reconfigured by re-training of the Neural Network, ideally with an electronic module of a same type and age, and based on injection devices of a same batch or age, as the electronic module and injection devices that had previously led to the deteriorating quality indicators. Adapted classifier and/or click identification parameter setting data may be transmitted or downloaded to the electronic module as a regular firmware update. The transmission of the adapted parameter settings, or of any other reconfiguration or firmware update information, may occur in encrypted form, based on any kind of shared secret exclusively accessible to the electronic module and its manufacturer. The predictive maintenance may also be applied in the case of an electronic delivery device with an embedded electronic unit for monitoring a repeated dispense of adjustable doses of medicament, despite the fact that event data sensing quality issues may be less pronounced in case of a sensing element embedded in the device.

In summary, it is a further objective of the disclosure to increase and improve an availability of the components for the generation of the delivery data from injection devices used by a patient in a self-administration therapy. This objective is achieved by a method of monitoring drug delivery from a drug delivery device by means of an associated electronic unit with at least one sensor, adapted to generate and handle subscription delivery of defined data and to transmit data items of the delivery data to a manufacturer of the electronic unit as a first (or subsequent) data subscriber, specifically comprising steps of predictive maintenance including proactively replacing or adapting the electronic unit well in advance of an anticipated failure. The electronic unit may be part of an electronic module for releasable attachment to a disposable injection device, and includes a sensor element for sensing a status of, or a process executed by means of, the injection device. Delivery event data sensed and determined by the electronic unit includes a dose of medicament dispensed by the injection device in a single delivery event and an event data sensing quality indicator or trust parameter indicative of an accuracy of the determined dose. Predictive maintenance may include the following steps, executed by or on behalf of the manufacturer of the electronic unit subscribing to defined data:

receiving first transmit data including a first quality indicator value for a first delivery event, and receiving second transmit data including a second quality indicator value for a second delivery event after the first event;

comparing, or evaluating, the two quality indicator values to determine, or extrapolate, a point of failure or insufficient accuracy of the electronic unit, and replacing the electronic unit, in particular the electronic module comprising the electronic unit, or adapting an operation of the electronic unit, before the point of failure is reached.

BRIEF DESCRIPTION OF THE DRAWINGS

The subject-matter of the disclosure will be explained in more detail in the following text with reference to exemplary embodiments as illustrated in the attached drawings, of which

For consistency, the same reference numerals are used to denote similar elements illustrated throughout the drawings.

DETAILED DESCRIPTION

Figure 1:
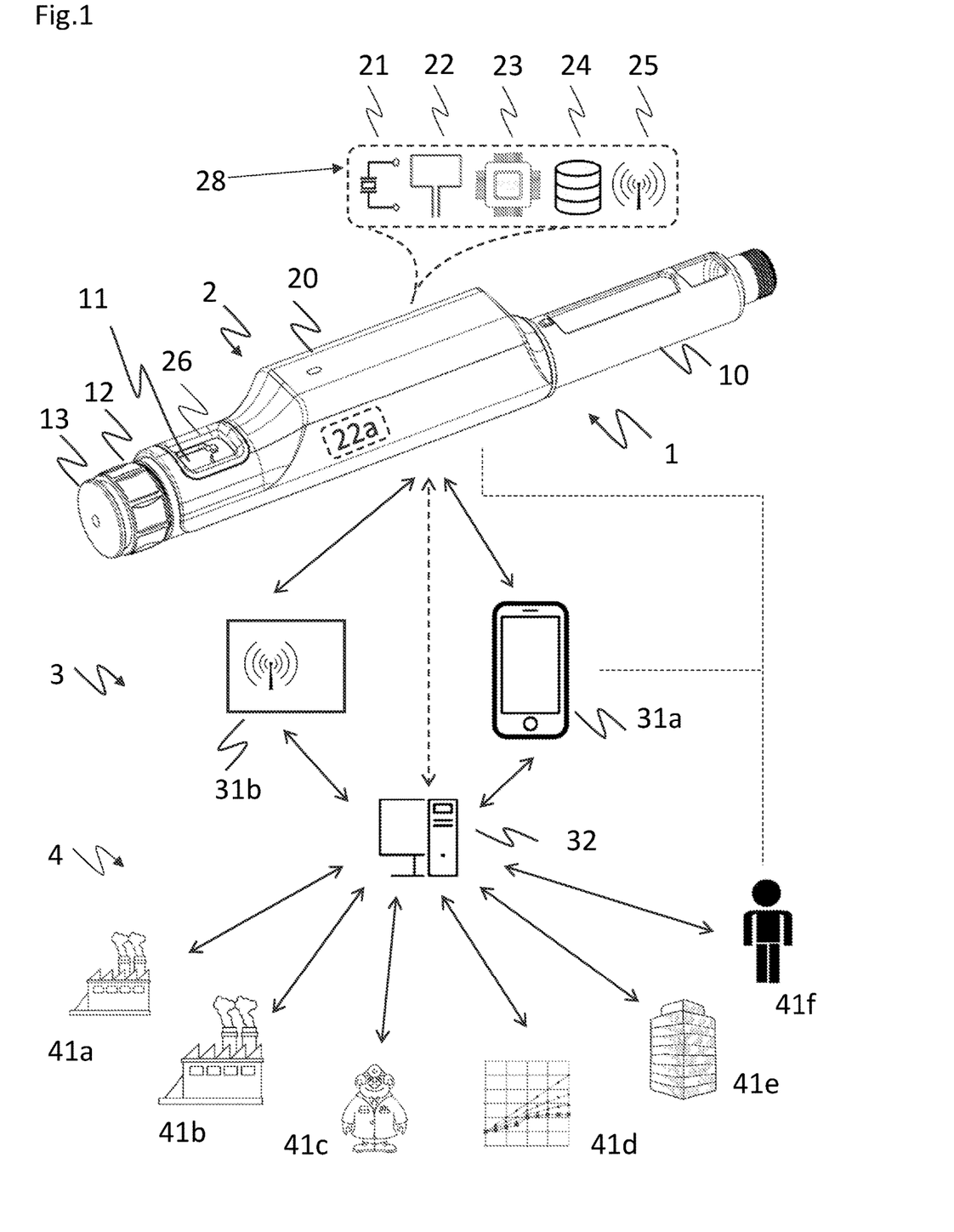
FIG. 1 depicts a medical injection monitoring and patient support system according to the present disclosure.

FIG. 1 depicts a medical injection or drug delivery monitoring and patient support system, comprising an injection device 1 in the form of a disposable, variable dose injection pen with manual drug dispense, an auxiliary electronic module 2 detachably mounted to the injection device, data transmission components 3, and data subscribers or system stakeholders 4.

The injection pen may include an elongate, pen-shaped device housing 10 which may essentially be symmetric around a main device axis, as well as a dosing device including a dosing sleeve 11, a rotary dosing knob 12, and a dispense or discharge button 13. The dosing knob 12 may enable the user to adjust a dose and is arranged on a proximal end of the dosing sleeve. The dosing sleeve 11 features markings in the form of numbers on its outer surface. When the dosing sleeve is screwed out of the housing during the dose setting operation, the adjusted dose may be displayed in a window of the housing. Alternatively, the injection device may be a disposable, single-dose auto-injector with a drive spring for automatic dispense of a dose of drug. A passive machine-readable tag (22a, shown in phantom in FIG. 1) may be mounted to, for instance embedded in or attached to a surface of, the device housing 10. The tag 22a may store drug information about the drug comprised in a container of the injection device, including any or all of a drug identifier, an expiry date, or a batch number of the drug.

The electronic module 2 may be laterally attached to the injection device 1 by means of a snap-fit or clip connection involving resilient module wings on opposite sides of the device housing. The housing 20 of the electronic module may feature a prominent laterally extending volume for accommodating the electronic unit 28, which may include a sensor element 21 to detect a status or signal from any kind of indicating component of the injection device, a tag reader 22 different from the injection sensor, for reading drug information from the machine-readable tag 22a, a processor 23, a data storage or memory 24 connected to the processor, and a transmitter 25 for wireless transmission of data about the injection progress via Bluetooth Low Energy (BLE) or equivalent short or near range wireless communication technology to the data transmission components 3. The electronic module 2 may further include a connection and system status indicator 26 that provides visual feedback about a connection status indicative of an established communication or transmission link to the components 3, and about a device, module, or process status including for instance an availability of battery power, a readiness of communication or transmitter means, an attached/detached status of the electronic module 2 and the injection device, or a progress of an ongoing injection process. The electronic module may be further adapted to produce a time-stamp indicating at what date and time a monitored dose has been injected, and to store at least the dose expelled and the time-stamp in the data storage unit for later upload. Alternatively, the electronic module 2 may start a timer or counter upon completion of an injection, from which an absolute time of the injection may be inferred at or following data upload.

The network or data transmission components 3 may include a mobile device 31a such as a smartphone or tablet device running a dedicated application program, or a laptop computer configured accordingly. Alternatively, the transmitter 25 of the electronic module 2 may communicate with a stationary medical gateway device 31b. The mobile or gateway device may be connected, via a 4G/LTE cellular mobile and/or wire-based communication network, to a remote, distributed cloud based computing facility or data server 32. Alternatively, the transmitter 25 of the electronic module may communicate directly with the data server 32 via wireless long-range communication networks such as 5G cellular mobile networks. The data server 32 may be configured to store delivery data, drug information, patient adherence data, or any further monitoring data accumulated by the electronic unit 28 and uploaded to the data server in encrypted format per subscriber as detailed below. The data server 32 may in turn forward the uploaded data to the data subscribers 4, which may include any or all of a device manufacturer 41a, a drug supplier or pharmaceutical company 41b, a healthcare professional HCP 41c assigned to a patient, a clinical research organization CRO 41d, a health insurance company 41e of the patient, and the patient himself 41f. The patient 41f may in addition, or alternatively, receive information from the visual indicator 26 of the electronic module, and/or from the mobile device 31a. The drug delivery monitoring system may include further intermediary network components or nodes in the communication paths between the mobile or gateway device and the data server, as well as between the latter and the data subscriber.

Figure 2:
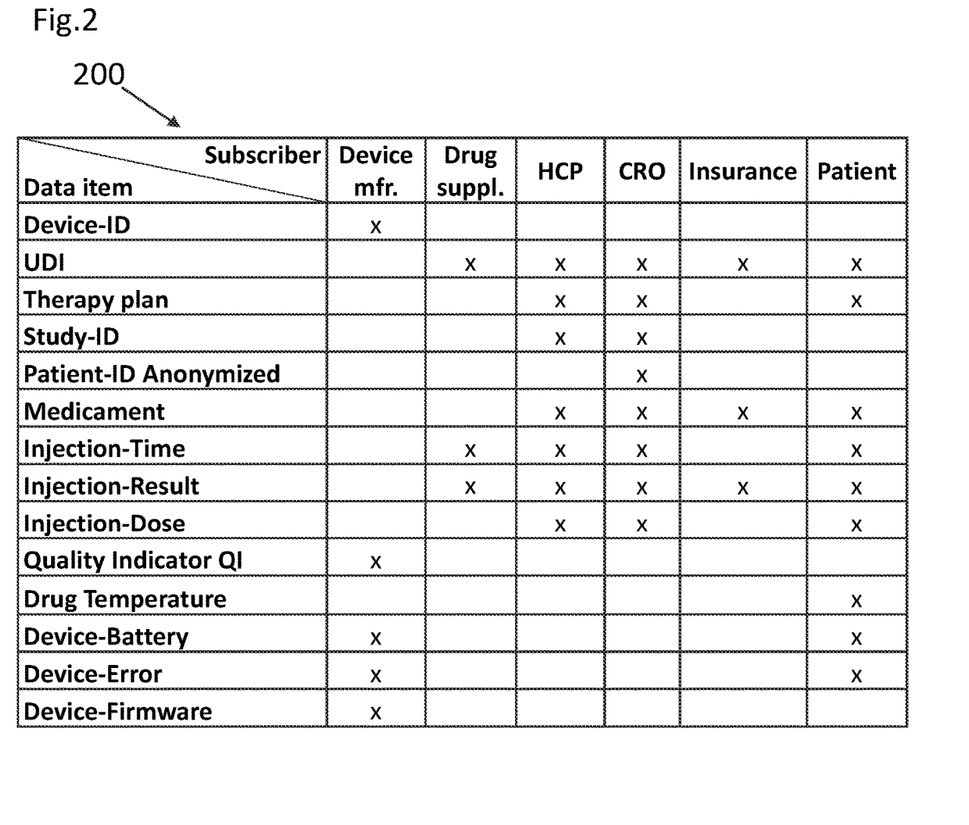
FIG. 2 is a an example of a consolidated representation of data-to-subscriber allocation schemes, according to the present disclosure.

FIG. 2 depicts a data structure 200, for example in the form of a consolidated allocation table or array, with an exemplary selection of delivery data items, in the first column, and an exemplary number of data subscribers in the first row. The crosses in a column of the table indicate to which delivery data items the respective subscriber has subscribed, such that each column represents a data allocation scheme according to the terminology used. The list of subscribers includes, in order, a device manufacturer, a drug supplier or pharmaceutical company, a healthcare professional (HCP) assigned to a patient, a clinical research organization (CRO), a health insurance of the patient, and the patient himself/herself. The device manufacturer may be the manufacturer of the auxiliary electronic module 2 including the electronic unit 28, the manufacturer of the delivery device to which the electronic module attaches, or the manufacturer of an electronic delivery device embedding the electronic unit 28.

The data items may include an identifier (ID) or serial number of the auxiliary electronic module or the electronic delivery device provided by the device manufacturer, the value of which is stored in a memory of the device upon device manufacturing. The delivery data items may further include a Unique Device Identification (UDI) including information on the drug, drug batch, drug expiry in encoded format; a therapy plan including the agreed medication schedule and configured device behavior; a clinical study identifier (ID); a patient identifier in anonymized form, and a designation or trade name of the medicament in plain text. All the aforementioned data may be provided on a tag 22a of the delivery device that may be read by a tag reader 22 of the auxiliary electronic module, or stored in a memory of the electronic delivery device or unit following download from a central server facility. The data items also may include event data of a specific delivery event such as a time of delivery, place of delivery, dispensed dose, and holding time elapsed between completion of drug dispense and removal of the delivery device from the injection site. The event data may further include an injection result in binary form or including an event data sensing quality indicator indicative of a level of quality of, or uncertainty tied to, the event data. Likewise, a drug temperature or further event parameter may be included. The data items ultimately may include further device data such as error, firmware, software, and battery status information of the auxiliary module or electronic delivery device.

As is evident from the table, the device manufacturer has subscribed to data items relating to the device, in order to track a lifecycle of the device. A usage time or usage count as a consolidated number of successfully completed delivery events may also be of interest to a manufacturer of an electronic delivery device, especially in view of complaint handling processes. It is also apparent from the table that the physician or other HCP of the patient, the healthcare insurance, and a CRO are all interested in event data including medication, dose, and delivery success. However, while the physician and CRO require to know the delivery result per patient and per event, the insurance may be satisfied with anonymized data allowing to establish therapy efficiency, and/or patient adherence to therapy plans.

Figure 3:
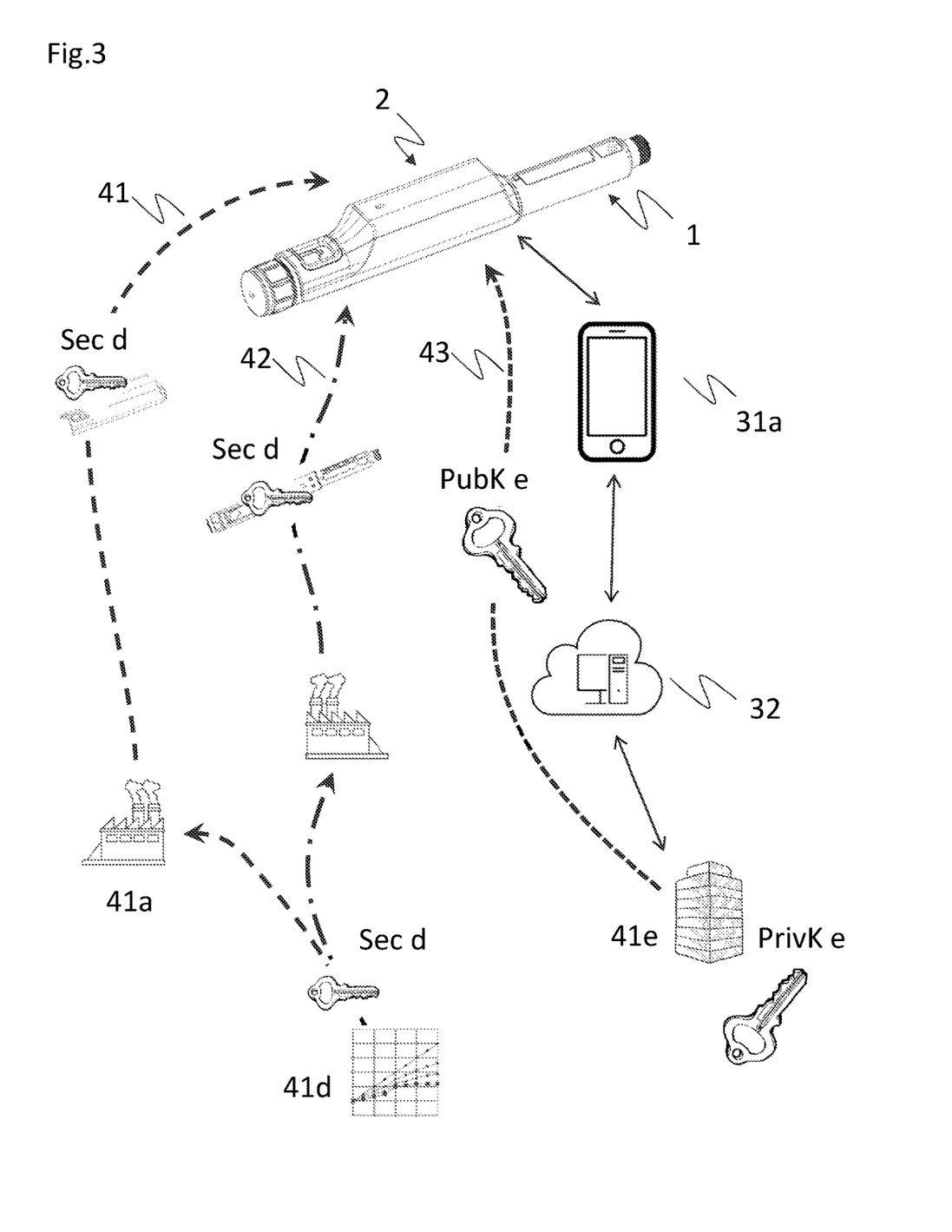
FIG. 3 illustrates three variants of subscriber-based encryption key provision, according to the present disclosure.

FIG. 3 illustrates three distinct variants of subscriber-based encryption key provision or distribution. In a first variant (first communication path represented by left-side curved arrow 41), exemplary first data subscriber 41d provides an encryption key or shared secret (Sec d) to the manufacturer 41a of electronic modules. The manufacturer then copies this key to a memory of each assembled electronic module 2. In a sub-variant, the manufacturer assembles electronic, or intelligent, delivery devices with embedded electronic units, in which case the key is copied to a memory of the electronic unit 28 of the electronic delivery device. In a second variant (second communication path represented by center curved arrow 42), the encryption key or shared secret (Sec d) of the first data subscriber 41d is provided to a delivery device end-assembly site, where the key may be copied to a machine-readable tag or label of each assembled delivery device 1. In a third variant (third communication path represented by right-side curved arrow 43), exemplary second subscriber 41e provides a public key (PubK e) via an exemplary communication network including the data transmission components 32, 31a to the electronic module 2 or, in a sub-variant, to an electronic delivery device. The three variants may be used in parallel or consecutively with one and the same auxiliary electronic device and/or data subscriber.

In an embodiment of variant two, the machine-readable tag 22a may be attached externally to the device housing, which may be compatible with non-transparent device housings, and which specifically may exclude embedding the tag 22a into the device housing in a molding step of the device housing preceding an assembly of the injection device. Attaching the tag 22a to the device housing surface may allow delaying of a programming or printing of the tag to a very late stage, specifically to finalize the tag during or even after assembly of the drug container and the injection device, yet still before attachment of the tag to the device housing. The passive machine-readable tag may include an optical bar code or a data-matrix/QR code label, or a non-optical Radio Frequency Identification (RFID) tag or transponder, specifically a NFC tag operating according to one of the Near-Field Communication (NFC) standards. Accordingly, the electronic module may be equipped with a camera or with an RFID/NFC reading or readout unit.

At least the standardized Near-Field Communication (NFC) tags may contain data including unique tag identifiers such as serial numbers encoded in the tag at the time of tag manufacture in read-only format such that this information cannot be altered once set. NFC tags may further include a user memory programmable, or writable, at delivery device assembly and providing for at least 300 Bytes of memory space, which is sufficient to store drug information in addition to an exemplary encryption key of 256 Bytes such as according to the RSA2048 encryption scheme. Near-field communication may use magnetic induction between two loop antennas connected to respective RFID chips or control units, and located within a near field of each other, thus effectively forming an air-core transformer operating at an exemplary frequency of 13.56 MHz well below an UHF band of 300 MHz or higher. In passive communication mode, the initiator device may provide a carrier field and the target device responds by modulating the existing field. In this mode, the target device may draw its operating power from the initiator-provided electromagnetic field. In the context of the present disclosure, the initiator may be an electronic unit 28 as part of the electronic module, and the target may be the passive tag 22a or transponder attached to the medicament delivery device housing.

The electronic unit 28 being integrated in the electronic injection device or being part of an electronic module may comprise a visual, audible and/or tactile status indicator indicating to a user a status of the system. The status of the system may include any of a device status of the injection device, a module status of the electronic module, or a delivery status of a drug dispensing process. The status indicator may be simple and limited to a few Light Emitting Diodes LEDs in traffic-light colors and/or an audible signal generator for generating language-independent beep sounds or simple melodies in accordance with a therapy plan to be followed. In an embodiment, the status information may include a positive confirmation of a dose having been set or corrected, or an indication about a lapse of a minimum holding, delay, or dwell time following completion of a substance dispensing activity to inform the user that it is now safe to remove the injection device. The status indicator may explicitly exclude any advanced human-machine interfacing capability, and be limited to a few, for example, specifically less than ten, messages conveyable to the user. In particular, the electronic unit 28 may not be wired to, and the electronic module may be free of, a display, screen, or projector for visually transmitting readable instructions, and likewise exclude an artificial speech assistant for reading out loud the instructions.

Figure 4:
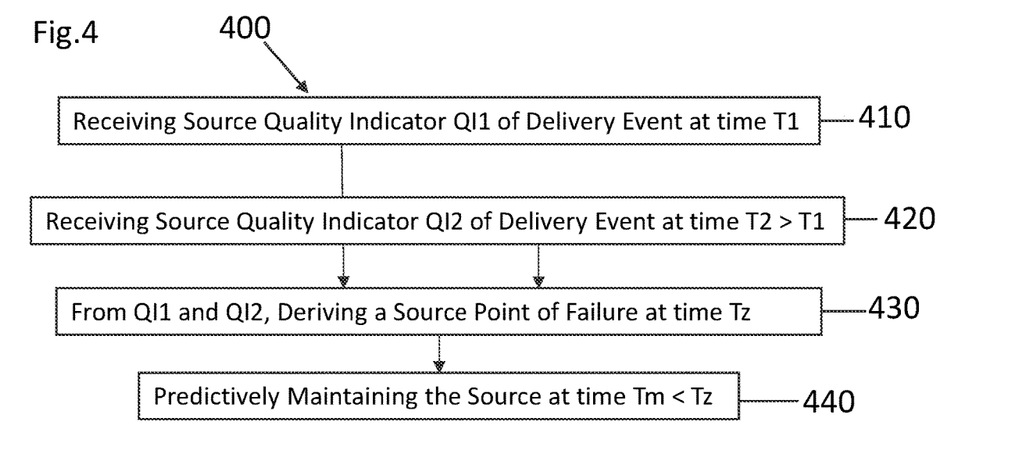
FIG. 4 is a flow chart of a method of predictively maintaining the system, according to the present disclosure.

FIG. 4 is a flow chart of an exemplary method 400 of predictively maintaining the above monitoring system, according to the present disclosure. The method includes the step of receiving a first source quality indicator value Q1 indicative of an accuracy of a dispensed dose determined by the electronic unit 28 in a first or earlier delivery event at time T1 (operation 410). The method includes the step of receiving a second source quality indicator value Q2 indicative of an accuracy of a dispensed dose determined by the electronic unit 28 in a second or later delivery event at time T2 (operation 420). The quality indicator source may be any of the components involved in the dose determination, including an electronic unit comprising sensor and processor elements, a reusable electronic module or delivery device hosting the electronic unit, or a disposable injection device to which the electronic unit is releasably attached. The method includes the step of evaluating the quality indicator values to derive, by statistical and predictive means, a source point of failure as a point in time Tz when a dose determination will no longer be possible or useful (operation 430). The quality indicator values are received and evaluated by or on behalf of a manufacturer of the source, e.g., unit. The method includes the step of predictively maintaining the source at a maintenance time Tm well before Tz, which includes intelligently alerting users and/or service personnel that the source is (or may be) operating abnormally and requires component replacement or process reconfiguration of the source devices (operation 440). While the device and method have been described in detail in the drawings and foregoing description, such description is to be considered illustrative or exemplary and not restrictive. Variations to the disclosed embodiments can be understood and effected by those skilled in the art and practicing the claimed subject matter, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims shall not preclude the existence of further meaningful combinations of these elements or steps.

LIST OF REFERENCE NUMERALS 1 injection device
10 device housing
11 dosing sleeve 12 dosing knob
13 dispense button
2 electronic module
20 module housing
21 sensor element
22 tag reader
22a machine-readable tag
23 processor
24 memory
25 transmitter
26 visual indicator
28 electronic unit
3 data transmission components
31a mobile device
31b gateway
32 data server
4 data subscribers
41 first communication path
42 second communication path
43 third communication path
200 data structure
400 flowchart of predictive maintenance
410, 420, 430, 440 steps in flowchart 400

What is claimed is:

1. An electronic unit for use with a drug delivery device and adapted to generate and handle drug delivery data of the delivery device and to transmit data items of the delivery data to a first data subscriber and to a second data subscriber, respectively, the electronic unit comprising:
    a housing configured to removably attach to the drug delivery device;
    at least one sensor arranged in the housing and communicatively coupled to the drug delivery device, the at least one sensor configured for collecting the delivery data associated therewith; and
    a processor with associated memory arranged in the housing and communicatively coupled to the at least one sensor, the processor having:
    access to a first encryption key and a second encryption key associated with the first data subscriber and the second data subscriber, respectively, and
    access to a first data allocation scheme and to a second data allocation scheme indicating to which delivery data item or items the first data subscriber and second data subscriber have respectively subscribed;
    wherein, upon receipt of the delivery data from the sensor, the processor of the electronic unit is configured:
    to prepare first transmit data including at least one delivery data item according to the first data allocation scheme defining a first subset of delivery data, and to encrypt the first transmit data based on the first encryption key;
    to prepare second transmit data including at least one delivery data item according to the second data allocation scheme defining a second subset of delivery data different from the first subset and to encrypt the second transmit data based on the second encryption key; and
    to cause transmission of the encrypted first transmit data and the encrypted second transmit data to the first data subscriber and the second data subscriber, respectively.

2. The electronic unit according to claim 1, wherein the drug delivery device comprises a disposable injection device generating signals that are detectable by the at least one sensor of the electronic unit, and wherein the injection device comprises a machine-readable tag storing the first encryption key of the first data subscriber, wherein the at least one sensor comprises a tag reader for reading the first encryption key from the machine-readable tag.

3. The electronic unit according to claim 1, wherein the processor is configured:
    to encrypt the first transmit data based on the first encryption key by encrypting the delivery data items with the first encryption key, or by encrypting the delivery data items with a generic key and encrypting the generic key with the first encryption key; and
    to control transmission of the encrypted first transmit data by transmitting the encrypted delivery data items or by transmitting the encrypted delivery data items and the encrypted generic key, respectively.

4. The electronic unit according to claim 1, wherein the memory is configured for storing the first encryption key and second encryption key and the first data allocation scheme and second data allocation scheme.

5. The electronic unit according to claim 4, wherein the first data allocation scheme assigns delivery data items including an identifier and a battery level of the electronic unit to a manufacturer of the electronic unit.

6. The electronic unit according to claim 1, further comprising a transmitter communicatively coupled to the processor and configured for communicating with a mobile device or with a stationary gateway device to transmit the encrypted first transmit data and encrypted second transmit data to a remote data server.

7. The electronic unit according to claim 1 further comprising:
    wherein the at least one sensor is a sensor for sensing data for deriving a quality indicator QI indicative of data accuracy of data determined by the electronic unit in a delivery event, wherein QI includes a first quality indicator value QI1 for a first delivery event and a second quality indicator value QI2 for a second delivery event after the first delivery event; and
    a transmitter for communicating the first quality indicator value QI1 and the second quality indicator value QI2 to at least one of the first data subscriber or the second data subscriber.

8. The electronic unit according to claim 1:
    wherein the at least one sensor comprises means for sensing two concurrent sensor signals from two distinct sensors, and
    further comprising a transmitter communicatively coupled to the processor and configured for communicating the two concurrent sensor signals to at least one of the first data subscriber or the second data subscriber.

9. The electronic unit according to claim 1 wherein the first data allocation scheme and the second data allocation scheme comprise a representation of data-to-subscriber allocation schemes in the form of a chart or array.

10. The electronic unit according to claim 1 wherein the at least one sensor comprises a tag reader for a machine-readable tag or label storing drug information mounted to a device housing of the drug delivery device.

* * * * *